(12) United States Patent
Chojin et al.

(10) Patent No.: US 8,702,737 B2
(45) Date of Patent: Apr. 22, 2014

(54) SURGICAL FORCEPS

(75) Inventors: Edward M. Chojin, Boulder, CO (US); Weng-Kai K. Lee, Longmont, CO (US)

(73) Assignee: Covidien LP, Mansfield, MA (US)

( * ) Notice: Subject to any disclaimer, the term of this patent is extended or adjusted under 35 U.S.C. 154(b) by 242 days.

(21) Appl. No.: 13/204,841

(22) Filed: Aug. 8, 2011

(65) Prior Publication Data
US 2013/0041402 A1      Feb. 14, 2013

(51) Int. Cl.
*A61B 17/32* (2006.01)
*A61B 17/00* (2006.01)
*A61B 18/18* (2006.01)

(52) U.S. Cl.
USPC .............. 606/167; 606/51; 606/174; 606/205

(58) Field of Classification Search
USPC ........ 606/39, 45, 167, 174, 204–208; 30/113, 30/120.3, 177, 272.1, 335
See application file for complete search history.

(56) References Cited

U.S. PATENT DOCUMENTS

| | | | |
|---|---|---|---|
| D249,549 S | 9/1978 | Pike | |
| D263,020 S | 2/1982 | Rau, III | |
| D295,893 S | 5/1988 | Sharkany et al. | |
| D295,894 S | 5/1988 | Sharkany et al. | |
| D298,353 S | 11/1988 | Manno | |
| D299,413 S | 1/1989 | DeCarolis | |
| D343,453 S | 1/1994 | Noda | |
| D348,930 S | 7/1994 | Olson | |
| D349,341 S | 8/1994 | Lichtman et al. | |
| D354,564 S | 1/1995 | Medema | |
| D358,887 S | 5/1995 | Feinberg | |
| D384,413 S | 9/1997 | Zlock et al. | |
| 5,749,886 A * | 5/1998 | Abidin et al. | 606/182 |
| H1745 H | 8/1998 | Paraschac | |
| D402,028 S | 12/1998 | Grimm et al. | |
| D408,018 S | 4/1999 | McNaughton | |
| D416,089 S | 11/1999 | Barton et al. | |
| D424,694 S | 5/2000 | Tetzlaff et al. | |
| D425,201 S | 5/2000 | Tetzlaff et al. | |

(Continued)

FOREIGN PATENT DOCUMENTS

| CN | 201299462 | 9/2009 |
|---|---|---|
| DE | 2415263 | 10/1975 |

(Continued)

OTHER PUBLICATIONS

U.S. Appl. No. 08/926,869, filed Sep. 10, 1997, James G. Chandler.

(Continued)

*Primary Examiner* — Tuan V Nguyen

(57) ABSTRACT

A forceps includes first and second shaft members each having a jaw member disposed at a distal end thereof. The shaft members are moveable relative to one another between spaced-apart and approximated positions to move the jaw members between open and closed positions. A knife assembly is engaged within the second shaft member. The knife assembly includes an arm extending through a trough defined within the second shaft member and has a knife disposed at a distal end thereof. The arm is moveable between a first position, corresponding to a retracted position of the knife, wherein the arm defines an arched portion extending from the second shaft member, and a second position, wherein the arched portion defines a more linear configuration to elongated the arm distally to advance the knife between the jaw members to cut tissue grasped therebetween.

31 Claims, 6 Drawing Sheets

(56) References Cited

U.S. PATENT DOCUMENTS

| | | | |
|---|---|---|---|
| H1904 H | 10/2000 | Yates et al. | |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| D465,281 S | 11/2002 | Lang | |
| D466,209 S | 11/2002 | Bon | |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| D525,361 S | 7/2006 | Hushka | |
| D531,311 S | 10/2006 | Guerra et al. | |
| 7,131,970 B2 | 11/2006 | Moses et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swoyer et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| D649,249 S | 11/2011 | Guerra | |
| D649,643 S | 11/2011 | Allen, IV et al. | |
| 2007/0088356 A1* | 4/2007 | Moses et al. | 606/51 |
| 2011/0060356 A1 | 3/2011 | Reschke et al. | |

FOREIGN PATENT DOCUMENTS

| | | |
|---|---|---|
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 19946527 | 12/2001 |
| DE | 10045375 | 10/2002 |
| DE | 10 2004 026179 | 12/2005 |
| DE | 20 2007 009165 | 10/2007 |
| DE | 20 2007 009317 | 10/2007 |
| DE | 20 2007 016233 | 3/2008 |
| DE | 19738457 | 1/2009 |
| DE | 10 2008 018406 | 7/2009 |
| EP | 1159926 | 12/2001 |
| JP | 61-501068 | 9/1984 |
| JP | 6-502328 | 3/1992 |
| JP | 5-5106 | 1/1993 |
| JP | 5-40112 | 2/1993 |
| JP | 6-030945 | 2/1994 |
| JP | 6-121797 | 5/1994 |
| JP | 6-285078 | 10/1994 |
| JP | 6-343644 | 12/1994 |
| JP | 6-511401 | 12/1994 |
| JP | 7-265328 | 10/1995 |
| JP | 8-56955 | 3/1996 |
| JP | 8-317936 | 3/1996 |
| JP | 8-289895 | 5/1996 |
| JP | 8-252263 | 10/1996 |
| JP | 8-317934 | 12/1996 |
| JP | 9-10223 | 1/1997 |
| JP | 9-122138 | 5/1997 |
| JP | 10-24051 | 1/1998 |
| JP | 11-070124 | 5/1998 |
| JP | 10-155798 | 6/1998 |
| JP | 2000-102545 | 9/1998 |
| JP | 11-47150 | 2/1999 |
| JP | 11-169381 | 6/1999 |
| JP | 11-192238 | 7/1999 |
| JP | 11-244298 | 9/1999 |
| JP | 2000-342599 | 12/2000 |
| JP | 2000-350732 | 12/2000 |
| JP | 2001-8944 | 1/2001 |
| JP | 2001-29356 | 2/2001 |
| JP | 2001-128990 | 5/2001 |
| JP | 2001-190564 | 7/2001 |
| JP | 2001-3400 | 11/2001 |
| JP | 2002-528166 | 3/2002 |
| JP | 2003-245285 | 9/2003 |
| JP | 2004-517668 | 6/2004 |
| JP | 2004-528869 | 9/2004 |
| JP | 2011-125195 | 6/2011 |
| SU | 401367 | 11/1974 |
| WO | WO 00/36986 | 6/2000 |
| WO | WO 00/59392 | 10/2000 |
| WO | WO 01/15614 | 3/2001 |
| WO | WO 01/54604 | 8/2001 |
| WO | WO 2005/110264 | 11/2005 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, 6/920/00, Thomas P. Ryan.
U.S. Appl. No. 12/336,970, filed Dec. 17, 2008, Paul R. Sremeich.
U.S. Appl. No. 12/876,668, filed Sep. 7, 2010, Sara E. Anderson.
U.S. Appl. No. 12/895,020, filed Sep. 30, 2010, Jeffrey M. Roy.
U.S. Appl. No. 12/896,100, filed Oct. 1, 2010, Ryan Artale.
U.S. Appl. No. 12/897,346, filed Oct. 4, 2010, Ryan Artale.
U.S. Appl. No. 12/906,672, filed Oct. 18, 2010, Kathy E. Rooks.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, filed Dec. 30, 2010, John R. Twomey.
U.S. Appl. No. 13/006,538, filed Jan. 14, 2011, John W. Twomey.
U.S. Appl. No. 13/028,810, filed Feb. 16, 2011, Robert M. Sharp.
U.S. Appl. No. 13/030,231, filed Feb. 18, 2011, Jeffrey M. Roy.
U.S. Appl. No. 13/050,182, filed Mar. 17, 2011, Glenn A. Homer.
U.S. Appl. No. 13/072,945, filed Mar. 28, 2011, Patrick L. Dumbauld.
U.S. Appl. No. 13/080,383, filed Apr. 5, 2011, David M. Garrison.
U.S. Appl. No. 13/085,144, filed Apr. 12, 2011, Keir Hart.
U.S. Appl. No. 13/089,779, filed Apr. 19, 2011, Yevgeniy Fedotov.
U.S. Appl. No. 13/091,331, filed Apr. 21, 2011, Jeffrey R. Townsend.
U.S. Appl. No. 13/102,573, filed May 6, 2011, John R. Twomey.
U.S. Appl. No. 13/102,604, filed May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.

(56) References Cited

OTHER PUBLICATIONS

U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.
U.S. Appl. No. 13/179,919, filed Jul. 11, 2011, Russell D. Hempstead.
U.S. Appl. No. 13/179,960, filed Jul. 11, 2011, Boris Chernov.
U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John R. Twomey.
U.S. Appl. No. 13/185,593, filed Jul. 19, 2011, James D. Allen, IV.
U.S. Appl. No. 13/204,841, filed Aug. 8, 2011, Edward J. Chojin.
U.S. Appl. No. 13/205,999, filed Aug. 9, 2011, Jeffrey R. Unger.
U.S. Appl. No. 13/212,297, filed Aug. 18, 2011, Allan J. Evans.
U.S. Appl. No. 13/212,308, filed Aug. 18, 2011, Allan J. Evans.
U.S. Appl. No. 13/212,329, filed Aug. 18, 2011, Allan J. Evans.
U.S. Appl. No. 13/212,343, filed Aug. 18, 2011, Duane E. Kerr.
U.S. Appl. No. 13/223,521, filed Sep. 1, 2011, John R. Twomey.
U.S. Appl. No. 13/227,220, filed Sep. 7, 2011, James D. Allen, IV.
U.S. Appl. No. 13/228,742, filed Sep. 9, 2011, Duane E. Kerr.
U.S. Appl. No. 13/231,643, filed Sep. 13, 2011, Keir Hart.
U.S. Appl. No. 13/234,357, filed Sep. 16, 2011, James D. Allen, IV.
U.S. Appl. No. 13/236,168, filed Sep. 19, 2011, James D. Allen, IV.
U.S. Appl. No. 13/236,271, filed Sep. 19, 2011, Monte S. Fry.
U.S. Appl. No. 13/243,628, filed Sep. 23, 2011, William Ross Whitney.
U.S. Appl. No. 13/247,778, filed Sep. 28, 2011, John R. Twomey.
U.S. Appl. No. 13/247,795, filed Sep. 28, 2011, John R. Twomey.
U.S. Appl. No. 13/248,976, filed Sep. 29, 2011, James D. Allen, IV.
U.S. Appl. No. 13/249,013, filed Sep. 29, 2011, Jeffrey R. Unger.
U.S. Appl. No. 13/249,024, filed Sep. 29, 2011, John R. Twomey.
U.S. Appl. No. 13/251,380, filed Oct. 3, 2011, Duane E. Kerr.
U.S. Appl. No. 13/277,373, filed Oct. 20, 2011, Glenn A. Homer.
U.S. Appl. No. 13/277,926, filed Oct. 20, 2011, David M. Garrison.
U.S. Appl. No. 13/277,962, filed Oct. 20, 2011, David M. Garrison.
U.S. Appl. No. 13/293,754, filed Nov. 10, 2011, Jeffrey M. Roy.
U.S. Appl. No. 13/306,523, filed Nov. 29, 2011, David M. Garrison.
U.S. Appl. No. 13/306,553, filed Nov. 29, 2011, Duane E. Kerr.
U.S. Appl. No. 13/308,104, filed Nov. 30, 2011, John R. Twomey.
U.S. Appl. No. 13/308,147, filed Nov. 30, 2011, E. Christopher Orton.
U.S. Appl. No. 13/312,172, filed Dec. 6, 2011, Robert J. Behnke, II.
U.S. Appl. No. 13/324,863, filed Dec. 13, 2011, William H. Nau, Jr.
U.S. Appl. No. 13/337,699, filed Dec. 27, 2011, David A. Schechter.
U.S. Appl. No. 13/344,729, filed Jan. 6, 2012, James D. Allen, IV.
U.S. Appl. No. 13/355,829, filed Jan. 23, 2012, John R. Twomey.
U.S. Appl. No. 13/357,979, filed Jan. 25, 2012, David M. Garrison.
U.S. Appl. No. 13/358,136, filed Jan. 25, 2012, James D. Allen, IV.
U.S. Appl. No. 13/358,657, filed Jan. 26, 2012, Kim V. Brandt.
U.S. Appl. No. 13/360,925, filed Jan. 30, 2012, James H. Orszulak.
U.S. Appl. No. 13/369,152, filed Feb. 8, 2012, William H. Nau, Jr.
U.S. Appl. No. 13/400,290, filed Feb. 20, 2012, Eric R. Larson.
U.S. Appl. No. 13/401,964, filed Feb. 22, 2012, John R. Twomey.
U.S. Appl. No. 13/404,435, filed Feb. 24, 2012, Kim V. Brandt.
U.S. Appl. No. 13/404,476, filed Feb. 24, 2012, Kim V. Brandt.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.

(56) References Cited

OTHER PUBLICATIONS

Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. " Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report Ep 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 016911.5 extended dated Mar. 2, 2011.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870.1 dated Aug. 9, 2010.
Int'l Search Report EP 10 161596.1 dated Jul. 28, 2010.
Int'l Search Report EP 10 167655.9 dated Aug. 31, 2011.
Int'l Search Report EP 10 168705.1 dated Oct. 4, 2010.
In'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182019 dated Aug. 4, 2011.
Int'l Search Report EP 10 182022.3 dated Mar. 11, 2011.

(56) References Cited

OTHER PUBLICATIONS

Int'l Search Report EP 10 185386.9 dated Jan. 10, 2011.
Int'l Search Report EP 10 185405.7 dated Jan. 5, 2011.
Int'l Search Report EP 10 186527.7 dated Jun. 17, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 159771.2 dated May 28, 2010.
Int'l Search Report EP 11 161117.4 dated Jun. 30, 2011.
Int'l Search Report EP 11 161118.2 dated Oct. 12, 2011.
Int'l Search Report EP 11 164274.0 dated Aug. 3, 2011.
Int'l Search Report EP 11 164275.7 dated Aug. 25, 2011.
Int'l Search Report EP 11 167437.0 dated Aug. 8, 2011.
Int'l Search Report EP 11 168458.5 dated Jul. 29, 2011.
Int'l Search Report EP 11 173008.1 dated Nov. 4, 2011.
Int'l Search Report EP 11 179514 dated Nov. 4, 2011.
Int'l Search Report EP 11 180182.5 dated Nov. 15, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US03/28539 dated Jan. 6, 2004.
Int'l Search Report PCT/USO4/03436 dated Mar. 3, 2005.
Int'l Search Report PCT/USO4/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

* cited by examiner

SURGICAL FORCEPS

BACKGROUND

1. Technical Field

The present disclosure relates to a surgical forceps and, more particularly, to a surgical forceps including an integrated cutting mechanism for grasping, sealing and/or dividing tissue.

2. Background of Related Art

A forceps is a plier-like instrument which relies on mechanical action between its jaws to grasp, clamp and constrict vessels or tissue. Electrosurgical forceps utilize both mechanical clamping action and electrical energy to affect hemostasis by heating tissue and blood vessels to coagulate and/or cauterize tissue. Certain surgical procedures require more than simply cauterizing tissue and rely on the unique combination of clamping pressure, precise electrosurgical energy control and gap distance (i.e., distance between opposing jaw members when closed about tissue) to "seal" tissue, vessels and certain vascular bundles. Typically, once a vessel is sealed, the surgeon has to accurately sever the vessel along the newly formed tissue seal. Accordingly, many vessel sealing instruments have been designed which incorporate a knife or blade member which effectively severs the tissue after forming a tissue seal.

SUMMARY

In accordance with one embodiment of the present disclosure, a forceps is provided. The forceps includes first and second shaft members each having a jaw member disposed at a distal end thereof. One or both of the shaft members is moveable relative to the other about a pivot pin between a spaced-apart position and an approximated position to move the jaw members between an open position and a closed position for grasping tissue therebetween. A knife assembly is operatively engaged within the second shaft member. The knife assembly includes an arm extending through a longitudinal trough defined within the second shaft member. The arm has a knife disposed at a distal end thereof is engaged to the second shaft member at a proximal end thereof. The arm is moveable between a first position, corresponding to a retracted position of the knife, wherein the arm defines an arched portion that extends from the second shaft member, and a second position, wherein the arched portion defines a more linear configuration such that the arm is elongated distally to advance the knife to an extended position, wherein the knife extends between the jaw members to cut tissue grasped therebetween.

In one embodiment, the arm is biased toward the first position. Further, the arm may be formed from a leaf spring that is biased toward the first position.

In another embodiment, the trough of the second shaft member is configured to guide the arm as the arm is moved between the first and second positions.

In another embodiment, the arm is configured to longitudinally translate between the pivot pin and the second shaft member during movement of the arm between the first and second positions. In such a configuration, the pivot pin retains the arm within the trough during movement of the arm between the first and second positions.

In yet another embodiment, a distal end of the second shaft member defines a distally-tapered configuration to form a channel for guiding the knife from the second shaft member to between the jaw members upon movement of the arm from the first position to the second position.

In yet another embodiment, one or both of the jaw members includes a longitudinally-extending knife channel defined therein. The knife channel is configured to permit reciprocation of the knife therethrough to cut tissue grasped between the jaw members.

In still another embodiment, the pivot pin is configured to inhibit proximal translation of the knife beyond the retracted position.

In another embodiment, the arched portion of the arm defines an actuator that is selectively depressible to transition the arm between the first position and the second position. Further, the actuator may be configured to provide tactile feedback to the user as to the position of the knife relative to tissue.

In still yet another embodiment, the first and second shaft members each define U-shaped configurations. More specifically, the first shaft member defines an inner width larger than an outer width of the second shaft member such that the second shaft member is receivable within the first shaft member. In such an embodiment, in the spaced-apart position, the second shaft member is only partially received within the first shaft member, while, in the approximated position, the second shaft member is substantially received within the first shaft member.

In another embodiment, the first and second shaft members and/or the knife are formed via stamping.

In still another embodiment, each of the jaw members includes an electrically-conductive tissue sealing plate disposed thereon. One or both of the tissue sealing plates is adapted to connect to a source of electrosurgical energy for sealing tissue grasped between the jaw members.

Another embodiment of a forceps provided in accordance with the present disclosure includes first and second shaft members having U-shaped configurations and defining troughs extending longitudinally therethrough. Each shaft member has a jaw member disposed at a distal end thereof. The shaft members are coupled to one another about a pivot pin and are moveable relative to one another between a spaced-apart position and an approximated position to move the jaw members between an open position and a closed position. The first shaft member is configured to substantially receive the second shaft member within the trough thereof upon movement of the shaft members to the approximated position. A knife assembly is operatively engaged within the trough of the second shaft member. The knife assembly includes an arm disposed within and extending longitudinal through the trough of the second shaft member. The arm is engaged to the second shaft member at a proximal end thereof and extends distally through the trough and between the second shaft member and the pivot pin to a distal end thereof that is disposed distally of the pivot pin. The distal end of the arm has a knife engaged thereon. The arm is transitionable between an arched position corresponding to a retracted position of the knife, and an elongated position corresponding to an extended position of the knife, wherein the arm is elongated distally such that the knife extends between the jaw members to cut tissue grasped therebetween.

BRIEF DESCRIPTION OF THE DRAWINGS

Various embodiments of the subject instrument are described herein with reference to the drawings wherein.

DETAILED DESCRIPTION

Figure 1:
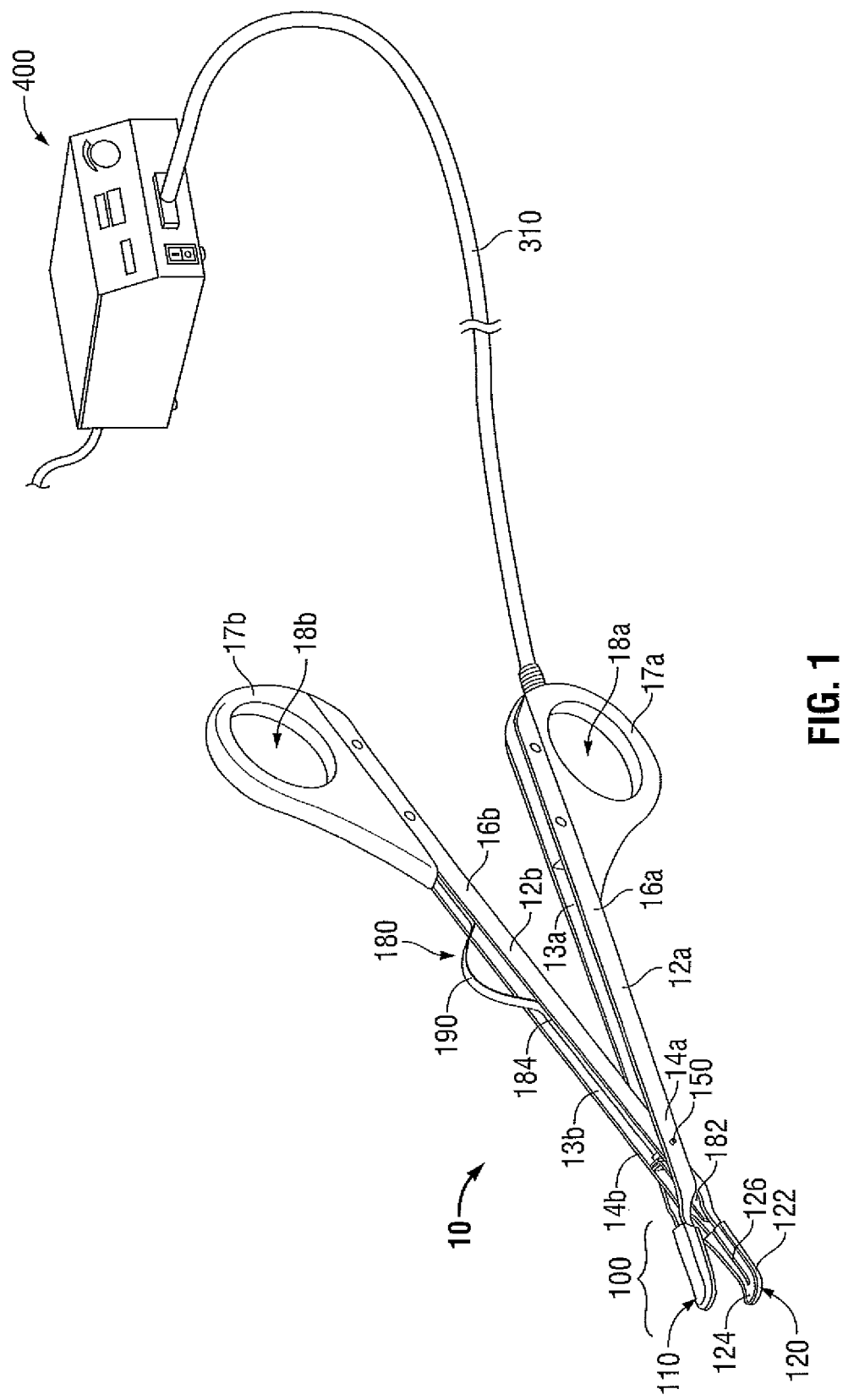
FIG. 1 is a side, perspective view of one embodiment of a forceps provided in accordance with the present disclosure, wherein jaw members of the forceps are disposed in an open position.

Embodiments of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

Figure 2:
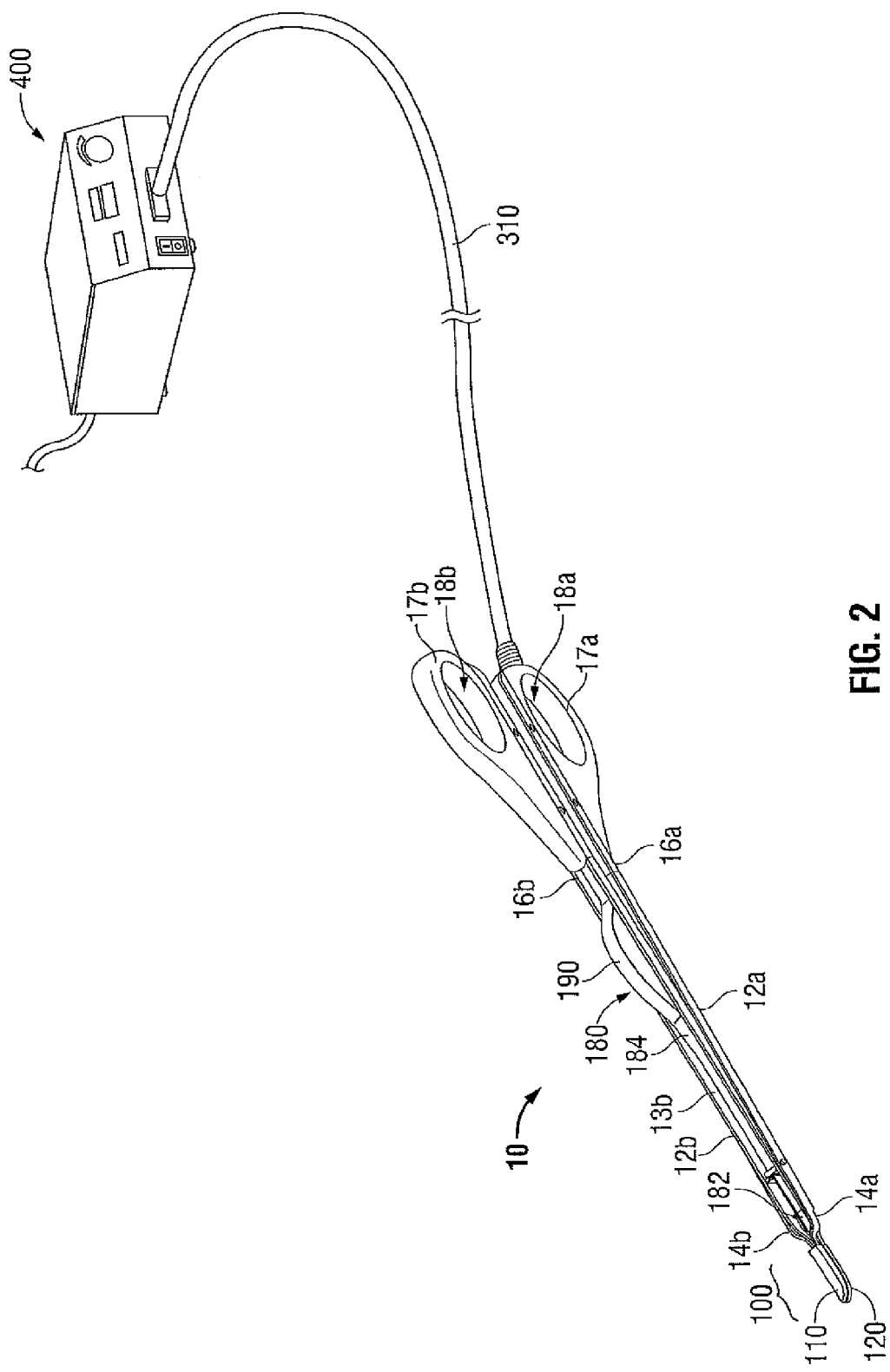
FIG. 2 is a side, perspective view of the forceps of FIG. 1, wherein the jaw members are disposed in a closed position.

Referring initially to FIGS. 1 and 2, an open surgical forceps 10 is shown including two elongated shaft members 12a and 12b each having a distal end 14a and 14b and a proximal end 16a and 16b, respectively. An end effector assembly 100 including opposing jaw members 110, 120, is attached to distal ends 14a and 14b of shaft members 12a and 12b, respectively. Opposing jaw members 110 and 120 are pivotably connected about a pivot pin 150 and are moveable relative to one another between an open position (FIG. 1) and a closed position (FIG. 2), upon movement of shaft members 12a and 12b between a spaced-apart position (FIG. 1) and an approximated position (FIG. 2), for grasping tissue therebetween. Further, as will be described below, a knife assembly 180 is operatively engaged with one of the shaft member, e.g., shaft member 12b, and includes a knife 182 configured for selective translation between jaw members 110, 120 to cut tissue grasped therebetween.

Each shaft member 12a and 12b includes a handle 17a and 17b disposed at the proximal end 16a and 16b thereof. Each handle 17a and 17b defines a finger hole 18a and 18b therethrough for receiving a finger of the user. As can be appreciated, finger holes 18a and 18b facilitate movement of shaft members 12a and 12b relative to one another which, in turn, pivots jaw members 110 and 120 between the open position (FIG. 1) and the closed position (FIG. 2), wherein the jaw members 110 and 120 cooperate to grasp tissue therebetween. Handles 17a, 17b may be formed from any suitable material and may be engaged to shaft members 12a, 12b, respectively, in any suitable configuration, e.g., via mechanical engagement (pin-aperture engagement, snap-fitting, etc.), molding, adhesion, etc. Alternatively, handles 17a, 17b may be monolithically formed with shaft members 12a, 12b, respectively.

Figure 3A:
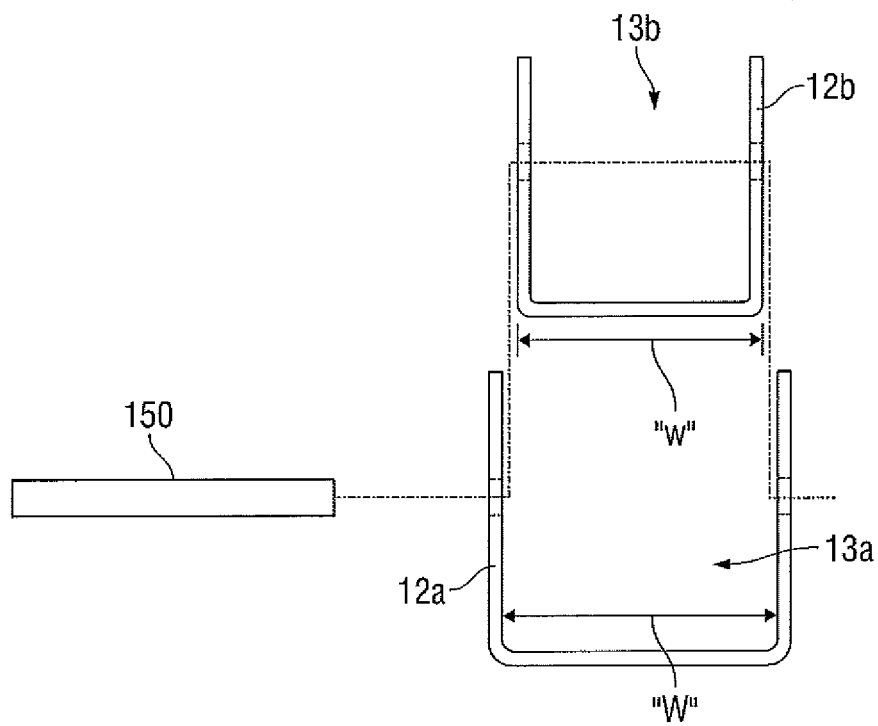
FIG. 3A is a transverse, cross-sectional view of shaft members of the forceps of FIG. 1, shown with parts separated.
Figure 3B:
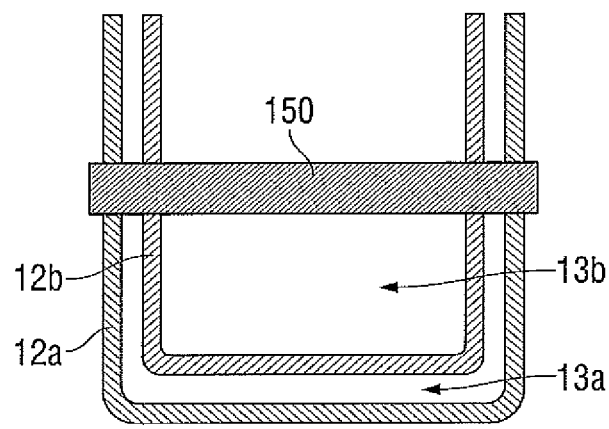
FIG. 3B is a transverse, cross-sectional view of the shaft members of the forceps of FIG. 1, shown in an assembled condition.

Referring now to FIGS. 3A-3B, in conjunction with FIGS. 1-2, shaft members 12a, 12b of forceps 10 each define a generally U-shaped configuration and are coupled to one another via pivot pin 150 towards distal ends 14a, 14b, respectively, thereof. U-shaped shaft members 12a, 12b may be formed from stainless steel, or any other suitable material, via any suitable manufacturing process. For example, shaft members 12a, 12b may be formed via stamping. Stamping is a relatively simple and inexpensive process and stamping stainless steel into U-shaped configurations to form shaft members 12a, 12b provides shaft members 12a, 12b with the required support and strength for effectively grasping tissue therebetween while maintaining a consistent closure pressure between jaw members 110, 120.

Continuing with reference to FIGS. 1-2 and 3A-3B, U-shaped shaft member 12a defines a trough 13a having a width "W" that is greater than a width "w" of U-shaped shaft member 12b such that shaft member 12b is receivable within trough 13a of shaft member 12a. In the spaced-apart position of shaft members 12a, 12b, as shown in FIG. 1, shaft member 12b is only partially received within trough 13a of shaft member 12a. However, upon movement of shaft members 12a, 12b to the approximated position to move jaw members 110, 120 to the closed position for grasping tissue therebetween, as shown in FIG. 2, shaft member 12b is substantially disposed within trough 13a of shaft member 12a. Such a configuration provides increased strength and inhibits lateral splay of shaft members 12a, 12b relative to one another when grasping tissue therebetween. Further, as will be described below, a trough 13b defined within U-shaped shaft member 12b, includes knife assembly 180 disposed therein.

Figure 4:
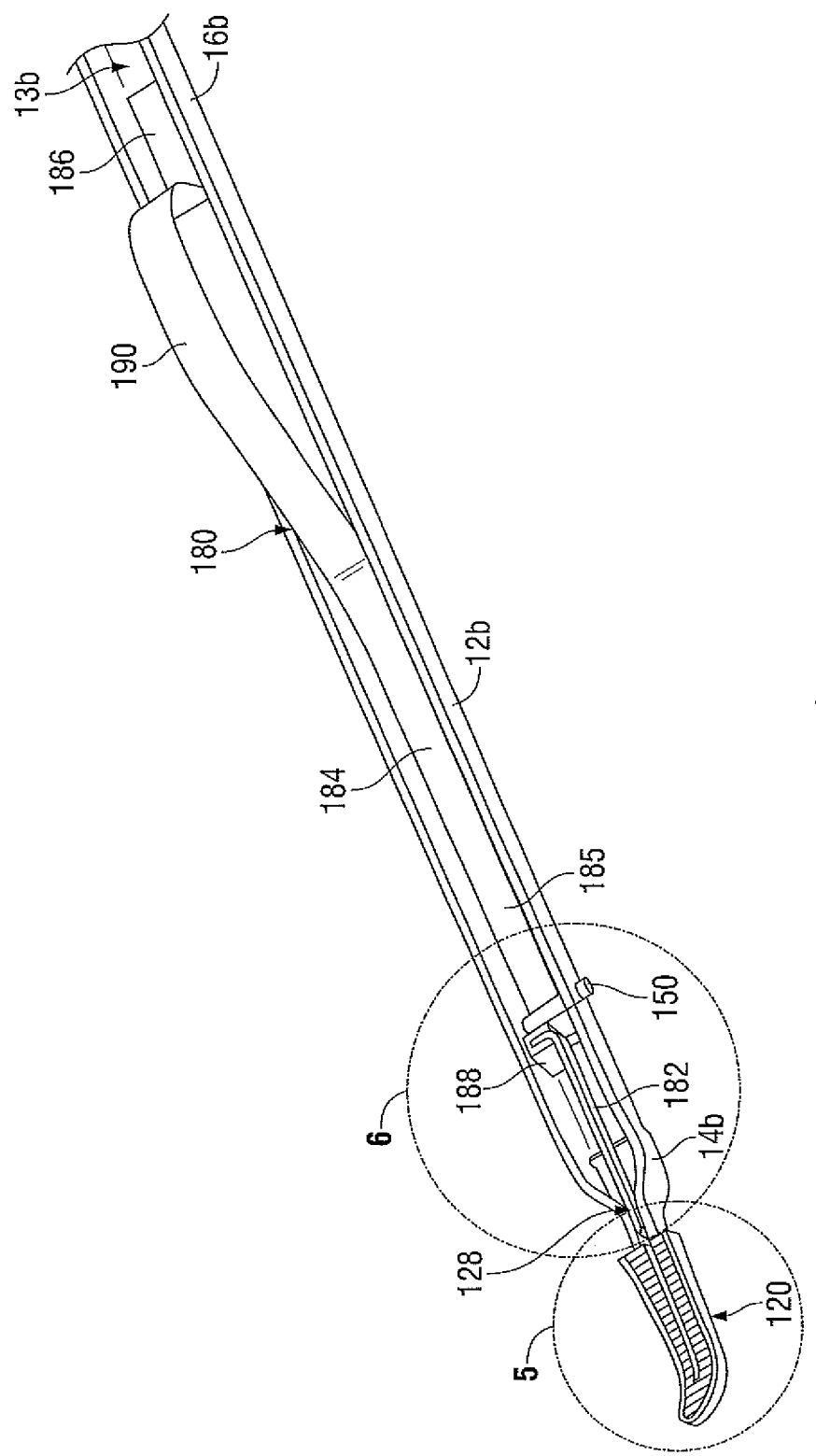
FIG. 4 is a top, perspective view of one of the shaft members of the forceps of FIG. 1.
Figure 5:
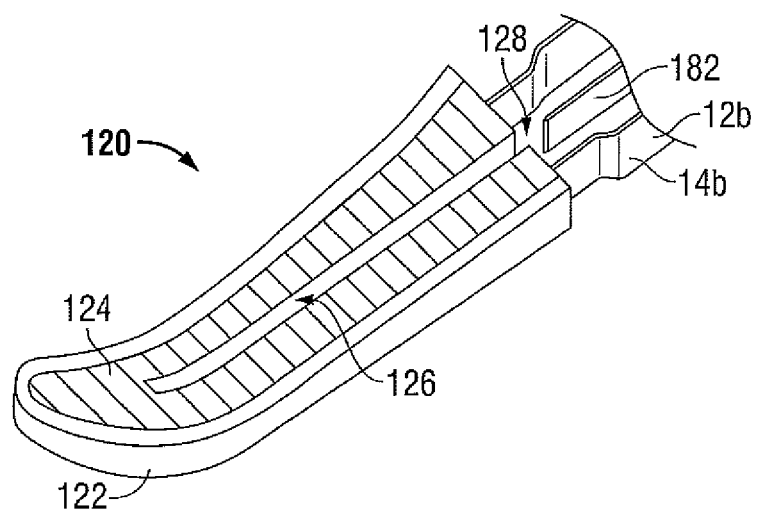
FIG. 5 is an enlarged, perspective view of the jaw member of the shaft member of FIG. 4.

Turning now to FIGS. 4-5, in conjunction with FIGS. 1-2, jaw member 120 is described. Jaw member 110 is substantially similar to jaw member 120 and, thus, will not be described herein for purposed of brevity. Jaw member 120 generally includes an insulative outer jaw housing 122 and an electrically-conductive tissue sealing plate 124 disposed on insulative outer jaw housing 122. Tissue sealing plate 124 is configured to oppose the tissue sealing plate (not shown) of jaw member 110 such that, upon movement of jaw members 110, 120 to the closed position, tissue is grasped between tissue sealing plate 124 and the tissue sealing plate (not shown) of jaw member 110. Tissue sealing plate 124 and/or the tissue sealing plate (not shown) of jaw member 110 is adapted to connect to a source of electrosurgical energy, e.g., generator 400, to seal tissue grasped between jaw members 110, 120. More specifically, an electrosurgical cable 310 may be coupled between generator 400 and one of the shaft members, e.g., shaft member 12a, such that energy may be transmitted from generator 400, along shaft member 12a, e.g., via wire(s) (not shown) extending through, or along shaft member 12a, or via any other suitable configuration, to end effector assembly 100 for conduction between tissue sealing plate 124 and the tissue sealing plate (not shown) of jaw member 110 and through tissue to seal tissue grasped therebetween. Further, a footswitch or handswitch (not shown) may be used to activate and/or control the supply of electrosurgical energy from generator 400 to tissue sealing plate 124 and/or the tissue sealing plate of jaw member 110.

Jaw member 120 further includes a longitudinally-extending knife channel 126 defined through tissue sealing plate 124. Knife channel 126 may be defined within one of jaw members 110, 120, e.g., jaw member 120, or may include channel halves defined within each of jaw members 110, 120 that cooperate with one another to form knife channel 126 upon movement of jaw members 110, 120 to the closed position. Knife channel 126 is configured to permit reciprocation of knife 182 of knife assembly 180 therethrough to cut tissue grasped between jaw members 110, 120.

With continued reference to FIGS. 1-2 and 4-5, jaw member 120 is engaged to shaft member 12b at distal end 14b thereof via any suitable engagement, e.g., molding, welding, friction-fitting, etc. More specifically, shaft member 12b defines a distally-tapered or narrowed configuration at distal end 14b thereof for engaging jaw member 120 thereon. The narrowed distal end 14b of shaft member 12b, as will be described below, defines a channel 128 positioned proximally of and aligned with knife channel 126 of jaw member 120 to guide translation of knife 182 of knife assembly 180 from trough 13b of shaft member 12b into knife channel 126 of jaw member 120 to cut tissue grasped between jaw members 110, 120.

Figure 6:
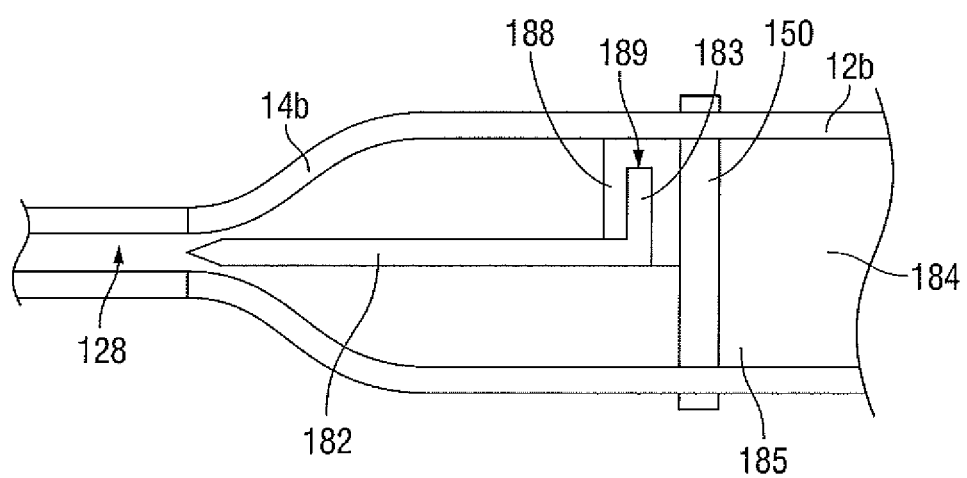
FIG. 6 is an enlarged, top view of a distal end of the shaft member of FIG. 5.

Referring now to FIGS. 4 and 6, in conjunction with FIGS. 1-2, knife assembly 180 is described. As mentioned above, knife assembly 180 is operatively engaged within trough 13b of shaft member 12b and includes a knife 182 that is selectively translatable through trough 13b, channel 128 defined within narrowed distal end 14b of shaft member 12b, and into knife channel 126 of tissue sealing plate 124 of jaw member 120 to cut tissue grasped between jaw members 110, 120. Knife assembly 180 includes an actuator arm 184, e.g., a leaf spring, disposed within trough 13b of shaft member 12b that engages knife 182 thereon at distal end 185 thereof. More specifically, proximal end 186 of actuator arm 184 is fixedly engaged within trough 13b of shaft member 12b at proximal end 16b of shaft member 12b, while actuator arm 184 extends distally therefrom through trough 13b, ultimately passing under pivot pin 150, i.e., actuator arm 184 extends between pivot 150 and the bottom surface of trough 13b of shaft member 12b, to engage knife 182 at distal end 185 thereof.

Knife 182 is engaged to actuator arm 184 via knife holder 188, distally of pivot pin 150. Knife holder 188 may be engaged to both knife 182 and actuator arm 184, which extends below pivot pin 150 distally thereof to engage knife holder 188, via any suitable engagement, e.g., friction-fitting, adhesion, welding, etc. More particularly, knife 182 may define a bent, or flanged proximal end 183 that is configured for engagement within a slot 189 defined within knife holder 188, although other configurations are contemplated. Further, stamping, or any other suitable manufacturing process, may be employed for forming knife 182 and the flanged configuration of proximal end 183 thereof, which facilitates engagement between knife 182 and knife holder 188. Stamping in particular is advantageous due to the relatively low cost of stamping, while the internal dimensions of channel 128 of shaft member 12b and knife channel 126 of tissue sealing plate 124 provide support to the stamped knife 182 by inhibiting lateral movement of knife 182 as knife 182 is translated therethrough.

Continuing with reference to FIGS. 4 and 6, knife 182 (and knife holder 188) is oriented generally-perpendicularly relative to actuator arm 184 such that, while actuator arm 184 is permitted to translate through trough 13b of shaft member 12b under pivot pin 150, knife 182 (and knife holder 188) is inhibited from translating proximally through trough 13b of shaft member 12b beyond pivot pin 150. As such pivot pin 150 functions as a proximal stop for knife 182.

Figure 7:
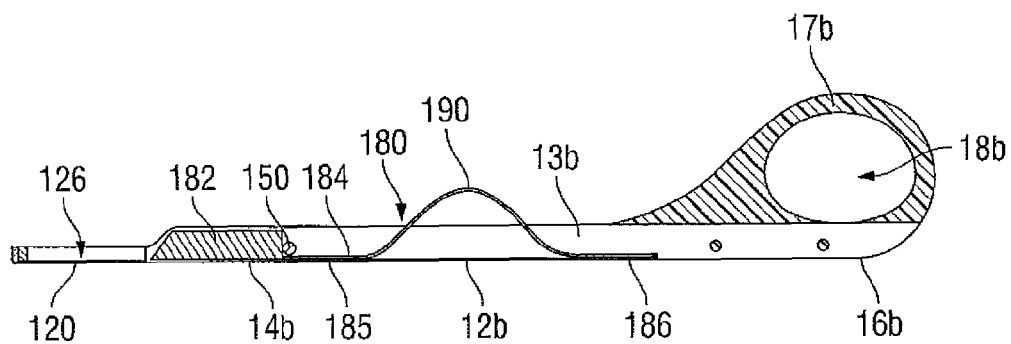
FIG. 7 is a longitudinal, cross-sectional view of the shaft member of FIG. 4 wherein a knife assembly thereof is disposed in a retracted position.

As best shown in FIG. 4, at least a portion of actuator arm 184 defines an arch-shaped configuration along at least a portion of the length thereof when at-rest. Actuator arm 184 may be formed as a leaf spring, or any other suitable biasing member than defines an arch-shaped configuration along at least a portion of the length thereof when at-rest. With actuator arm 184 disposed in this at-rest position, knife 182 is biased towards a retracted position, wherein knife 182 is disposed within trough 13b of shaft member 12b, proximally of jaw member 120. Pivot pin 150, as mentioned above, functions as a proximal stop, inhibiting further proximal translation of knife 182 through trough 13b of shaft member 12b and, thus, inhibiting further arching of actuator arm 184. As will be described in greater detail below, the arched portion of actuator arm 184 functions as an actuator 190 for selectively translating knife 182 relative to jaw member 120 between the retracted position (FIG. 7) and an extended position (FIG. 9), wherein knife 182 is advanced distally though trough 13b and channel 128 of shaft member 12b and into knife channel 126 defined within tissue sealing plate 124 of jaw member 120 to cut tissue grasped between jaw members 110, 120 (FIGS. 1-2).

Continuing with reference to FIG. 4, in conjunction with FIG. 6, depressing actuator 190, i.e., the arched portion of actuator arm 184, effects distal translation of knife 182 due to the engagement of knife 182 and actuator arm 184 at distal end 185 thereof and due to the fixed engagement of actuator arm 184 to shaft member 12b at proximal end 186 thereof, which inhibits proximal translation of actuator arm 184. More specifically, depression of actuator 190 urges the arched portion of actuator arm 184 against its bias towards a more linear configuration, i.e., depression of actuator 190 elongates actuator arm 184, thereby causing actuator arm 184 to elongated distally (since actuator arm 184 is inhibited from elongating proximally). Thus, as actuator 190 is depressed, actuator arm 184 is advanced distally under pivot pin 150 to translate knife 182 from the retracted position (FIG. 7), wherein knife 182 is disposed in close proximity to pivot pin 150, proximally of jaw member 120, to the extended position (FIG. 9), wherein knife 182 is translated distally from trough 13b of shaft member 12b, through channel 128 of shaft member 12b, and into knife channel 126 of tissue sealing plate 124 of jaw member 120 to cut tissue grasped between jaw members 110, 120 (FIGS. 1-2). Further, the width of actuator arm 184 may substantially similar to the width of trough 13b of shaft member 12b such that trough 13b guides the elongation of actuator arm 184 and inhibits lateral movement thereof, thereby helping to ensure smooth and consistent translation of knife 184 between the retracted and extended positions. Pivot pin 150 also helps guide the elongation of actuator arm 184 by helping to ensure that actuator arm 184 is retained within trough 13b of shaft member 12b, i.e., with actuator arm 184 passing between pivot pin 150 and shaft member 12b, pivot pin 150 inhibits substantial separation of actuator arm 184 from within trough 13b of shaft member 12b.

Turning now to FIGS. 1-2, and 4-9, the use and operation of forceps 10 is described. Initially, as shown in FIG. 1, shaft members 12a and 12b are moved to the spaced-apart position such that jaw members 110, 120, disposed at distal ends 14a, 14b, of shaft members 12a and 12b, respectively, are moved to the open position. In this position, as mentioned above, shaft member 12b is only partially received within trough 13a of shaft member 12a and actuator arm 184 remains disposed in the at-rest position defining arched portion, or actuator 190 extending from shaft member 12b. With jaw members 110, 120 disposed in the open position, as shown in FIG. 1, forceps 10 may be manipulated into position such that tissue to be grasped, sealed and/or divided is disposed between jaw members 110, 120.

Once tissue is positioned as desired, shaft members 12a and 12b may be moved toward one another, e.g., to the approximated position, to pivot jaw members 110, 120 about pivot pin 150 toward the closed position to grasp tissue between tissue sealing plate 124 of jaw member 120 and the tissue sealing plate (not shown) of jaw member 110, as shown in FIG. 2. As shaft members 12a, 12b are approximated relative to one another to close jaw members 110, 120, shaft member 12b is increasingly disposed within trough 13a of shaft member 12a, ultimately reaching the approximated position, wherein shaft member 12b is substantially disposed within trough 13a of shaft member 12a. With tissue grasped between jaw members 110, 120, the user may selectively apply electrosurgical energy from generator 400, e.g., via a footswitch or handswitch (not shown), through cable 310, and, ultimately, to electrically-conductive tissue sealing plate 124 of jaw member 120 and the tissue sealing plate (not shown) of jaw member 110 to seal tissue grasped between jaw members 110, 120.

Figure 8:
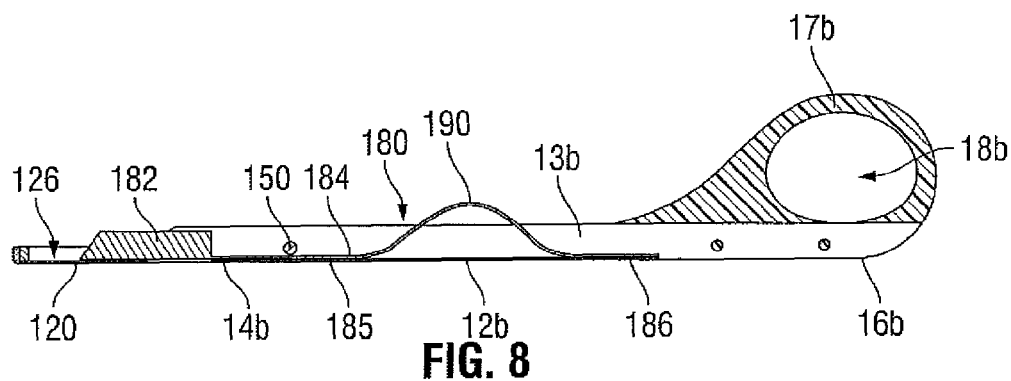
FIG. 8 is a longitudinal, cross-sectional view of the shaft member of FIG. 4, wherein the knife assembly is transitioning from the retracted position to an extended position.

Referring now to FIGS. 4-9, after sealing tissue, or where it is only desired to cut tissue grasped between jaw members 110, 120, the user may advance knife 182 through knife channel 126 of jaw member 120 to cut tissue grasped therebetween, e.g., to cut tissue along the previously-formed tissue seal. In order to advance knife 182 from the retracted position (FIG. 7) to the extended position (FIG. 9) to cut tissue, the user depresses actuator 190 of actuator arm 184. More specifically, the user depresses actuator 190, i.e., the arched portion of actuator arm 184, from the at-rest position shown in FIG. 7, wherein knife 182 is disposed in close proximity to pivot pin 150, i.e., the retracted position, such that actuator arm 184 is elongated distally. As actuator arm 184 is elongated distally, actuator arm 184 is advanced distally under pivot pin 150, as shown in FIG. 8, to translate knife 182 distally from trough 13b of shaft member 12b and into channel 128 defined by narrowed distal end 14b of shaft member 12b.

Figure 9:
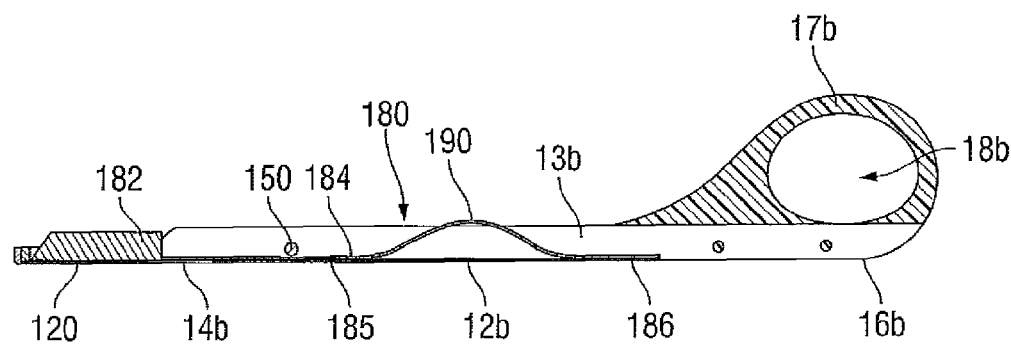
FIG. 9 is a longitudinal, cross-sectional view of the shaft member of FIG. 4, wherein the knife assembly is disposed in the extended position.

Further depression of actuator 190 translates knife 182 further distally through channel 128 of shaft member 12b and, ultimately, through knife channel 126 defined within tissue sealing plate 124 of jaw member 120 to the extended position, as shown in FIG. 9, for cutting tissue grasped between jaw members 110, 120 (FIGS. 1-2). As mentioned above, pivot pin 150 and trough 13b of shaft member 12b guide actuator arm 184 as actuator arm 184 is elongated distally, and the narrowed distal end 14b of shaft member 12b and knife channel 126 guide the distal translation of knife 182 into and through knife channel 126 of jaw member 120, thus helping to ensure smooth and consistent reciprocation of knife 182 between the retracted and extended positions. Further, as the user depresses actuator 190 of actuator arm 184 to advance knife 182, the user is provided with tactile feedback as to the resistance encountered by knife 182. In other words, as knife 182 is advanced into contact with tissue grasped between jaw members 110, 120 (FIGS. 1-2), knife 182 is met with resistance by the tissue, the resistance being transferred along actuator arm 184 to urge actuator arm 184 back toward the at-rest position. The urging of actuator arm 184 back towards the at-rest position urges actuator 190 back toward the arched configuration, which can be felt by the user. As such, the user is alerted to the relative position of knife 182, e.g., whether knife 182 has yet to contact tissue (no substantial resistance), whether knife 182 is currently contacting or being advanced through tissue (relatively greater resistance), and/or whether knife 182 has been advanced completely through tissue (relatively less resistance), based upon the tactile feedback received from actuator 190.

Once knife 182 has been advanced through tissue to cut tissue, knife 182 may be returned to the retracted position. To return knife 182 to the retracted position, actuator 190 is released, allowing actuator arm 184 to translate proximally under pivot pin 150, ultimately returning under bias back to the at-rest position defining the arched portion therealong. As actuator arm 184 is returned to the at-rest position, knife 182 is returned proximally within trough 13b of shaft member 12b and into abutment with, or in close proximity of pivot pin 150, which inhibits further proximal translation of knife 182 through trough 13b of shaft member 12b. With knife 182 disposed in the retracted position, shaft members 12a, 12b may be returned to the spaced-apart position such that jaw members 110, 120 are returned to the open position for removal of forceps 10 from the surgical site.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A forceps, comprising:
   first and second shaft members each having a jaw member disposed at a distal end thereof, at least one of the shaft members moveable relative to the other about a pivot pin between a spaced-apart position and an approximated position to move the jaw members between an open position and a closed position for grasping tissue therebetween; and
   a knife assembly operatively engaged within the second shaft members, the knife assembly including:
   an arm extending through a longitudinal trough defined within the second shaft member, the arm having a knife disposed at a distal end thereof and engaged to the second shaft member at a proximal end thereof, the arm moveable between a first position, corresponding to a retracted position of the knife, wherein the arm defines an arched portion that extends from the second shaft member, and a second position, wherein the arched portion defines a more linear configuration such that the arm is elongated distally to advance the knife to an extended position, wherein the knife extends between the jaw members to cut tissue grasped therebetween, wherein the arm is configured to longitudinally translate between the pivot pin and the second shaft member during movement of the arm between the first and second positions, the pivot pin configured to retain the arm within the trough during movement of the arm between the first and second positions.

2. The forceps according to claim 1, wherein the arm is biased toward the first position.

3. The forceps according to claim 1, wherein the arm is formed from a leaf spring.

4. The forceps according to claim 1, wherein the trough of the second shaft member is configured to guide the arm as the arm is moved between the first and second positions.

5. The forceps according to claim 1, wherein a distal end of the second shaft member is tapered distally to define a channel for guiding the knife from the second shaft member to between the jaw members upon movement of the aim from the first position to the second position.

6. The forceps according to claim 1, wherein at least one of the jaw members includes a longitudinally-extending knife channel defined therein, the knife channel configured to permit reciprocation of the knife therethrough to cut tissue grasped between the jaw members.

7. The forceps according to claim 1, wherein the pivot pin is configured to inhibit proximal translation of the knife beyond the retracted position.

8. The forceps according to claim 1, wherein the arched portion of the arm defines an actuator that is selectively depressible to transition the arm between the first position and the second position.

9. The forceps according to claim 8, wherein the actuator provides tactile feedback to the user as to the position of the knife relative to tissue.

10. The forceps according to claim 1, wherein the first and second shaft members each define U-shaped configurations, the first shaft member defining an inner width larger than an outer width of the second shaft member such that the second shaft member is receivable within the first shaft member.

11. The forceps according to claim 10, wherein, in the spaced-apart position, the second shaft member is only partially received within the first shaft member and wherein, in the approximated position, the second shaft member is substantially received within the first shaft member.

12. The forceps according to claim 1, wherein the shaft members are formed via stamping.

13. The forceps according to claim 1, wherein the knife is formed via stamping.

14. The forceps according to claim 1, wherein each of the jaw members includes an electrically-conductive tissue sealing plate disposed thereon, at least one of the tissue sealing plates adapted to connect to a source of electrosurgical energy for sealing tissue grasped between the jaw members.

15. A forceps, comprising:
first and second shaft members, each shaft member having a U-shaped configuration defining a trough extending longitudinally therethrough, each shaft member having a jaw member disposed at a distal end thereof, the shaft members coupled to one another about a pivot pin and moveable relative to one another between a spaced-apart position and an approximated position to move the jaw members between an open position and a closed position for grasping tissue therebetween, the first shaft member configured to substantially receive the second shaft member within the trough thereof upon movement of the shaft members to the approximated position; and
a knife assembly operatively engaged within the trough of the second shaft member, the knife assembly including:
an arm disposed within and extending longitudinal through the trough of the second shaft member, the arm engaged to the second shaft member at a proximal end thereof and extending distally through the trough and between the second shaft member and the pivot pin to a distal end thereof that is disposed distally of the pivot pin, the distal end of the arm having a knife engaged thereon, the arm transitionable between an arched position corresponding to a retracted position of the knife, and an elongated position corresponding to an extended position of the knife, wherein the arm is elongated distally such that the knife extends between the jaw members to cut tissue grasped therebetween, wherein the pivot pin is configured to inhibit proximal translation of the knife beyond the retracted position.

16. The forceps according to claim 15, wherein the arm is configured to longitudinally translate between the pivot pin and the second shaft member during movement of the arm between the arched and elongated positions.

17. The forceps according to claim 15, wherein, in the arched position, the arm defines an actuator that is selectively depressible to transition the arm from the arched position to the elongated position.

18. The forceps according to claim 17, wherein the actuator provides tactile feedback to the user as to the position of the knife relative to tissue.

19. A forceps, comprising:
first and second shaft members each having a jaw member disposed at a distal end thereof, at least one of the shaft members moveable relative to the other about a pivot pin between a spaced-apart position and an approximated position to move the jaw members between an open position and a closed position for grasping tissue therebetween; and
a knife assembly operatively engaged within the second shaft members, the knife assembly including:
an arm extending through a longitudinal trough defined within the second shaft member, the arm having a knife disposed at a distal end thereof and engaged to the second shaft member at a proximal end thereof, the arm moveable between a first position, corresponding to a retracted position of the knife, wherein the arm defines an arched portion that extends from the second shaft member, and a second position, wherein the arched portion defines a more linear configuration such that the arm is elongated distally to advance the knife to an extended position, wherein the knife extends between the jaw members to cut tissue grasped therebetween, wherein the pivot pin is configured to inhibit proximal translation of the knife beyond the retracted position.

20. The forceps according to claim 19, wherein the arm is biased toward the first position.

21. The forceps according to claim 19, wherein the arm is formed from a leaf spring.

22. The forceps according to claim 19, wherein the trough of the second shaft member is configured to guide the arm as the arm is moved between the first and second positions.

23. The forceps according to claim 19, wherein a distal end of the second shaft member is tapered distally to define a channel for guiding the knife from the second shaft member to between the jaw members upon movement of the arm from the first position to the second position.

24. The forceps according to claim 19, wherein at least one of the jaw members includes a longitudinally-extending knife channel defined therein, the knife channel configured to permit reciprocation of the knife therethrough to cut tissue grasped between the jaw members.

25. The forceps according to claim 19, wherein the arched portion of the arm defines an actuator that is selectively depressible to transition the arm between the first position and the second position.

26. The forceps according to claim 25, wherein the actuator provides tactile feedback to the user as to the position of the knife relative to tissue.

27. The forceps according to claim 19, wherein the first and second shaft members each define U-shaped configurations, the first shaft member defining an inner width larger than an outer width of the second shaft member such that the second shaft member is receivable within the first shaft member.

28. The forceps according to claim 27, wherein, in the spaced-apart position, the second shaft member is only partially received within the first shaft member and wherein, in the approximated position, the second shaft member is substantially received within the first shaft member.

29. The forceps according to claim 19, wherein the shaft members are formed via stamping.

30. The forceps according to claim 19, wherein the knife is formed via stamping.

31. The forceps according to claim 19, wherein each of the jaw members includes an electrically-conductive tissue sealing plate disposed thereon, at least one of the tissue sealing plates adapted to connect to a source of electrosurgical energy for sealing tissue grasped between the jaw members.

* * * * *